United States Patent
Ewers et al.

(10) Patent No.: US 6,428,803 B1
(45) Date of Patent: Aug. 6, 2002

(54) HYDROXYLAPATITE GEL

(76) Inventors: Rolf Ewers; Else Spassova, both of Schumanngasse 15, A-1180 Wien Österreich (DE); Margarita Nikolova Jordanova, Boul. Petko Todorov Bl. 3, Eing. A, App. 10, 1404 Sofia (BG); Dimitar Assenov Djerov, Dante-Strasse 6 Stredez-1000, Sofia (BG); Sava Assenov Dramov, Dianabad Bl. 4 App. 114 Isgrev-1172, Sofia (BG); Gueorgui Nikolov Kirov, Hadji Dimitar Bl, 140. Eing. B. App. 57 Produenc Sofia (BG); Velitchka Alexandrova Velichkova, Sveta Trioza Bl. 365 Eing. B. App. 55, 1309 Sofia (BG); Kiril Ranguelov Tchakalski, Kuponite-Strasse 20 Bl. 140, Vitoscha-1614, Sofia (BG); Andrey Ivanov Andreev, Boul. Vitoscha 41 Sredez-1000, Sofia (BG); Emil Stoimenov Ivanov, Rassadnika Bl. 9 Eing. B App. 46, 1330 Sofia (BG); Arnulf Baumann, Univ. Klinik für Mund-, Kieferund Gesichtschirurgie AKH Währinger Gürtel 18-20 A-1090, Wien Österreich (DE)

(*) Notice: Subject to any disclaimer, the term of this patent is extended or adjusted under 35 U.S.C. 154(b) by 0 days.

(21) Appl. No.: 09/451,691

(22) Filed: Nov. 30, 1999

Related U.S. Application Data

(63) Continuation of application No. PCT/EP98/03093, filed on May 26, 1998.

(51) Int. Cl.$^7$ ................................................ A61F 2/02
(52) U.S. Cl. ........................ 424/426; 623/16; 523/114; 523/115
(58) Field of Search ........................... 424/426; 623/16; 523/114, 115

(56) References Cited

U.S. PATENT DOCUMENTS 4,207,306 A * 6/1980 Jacrho ........................ 423/633

* cited by examiner

*Primary Examiner*—Carlos A. Azpuru
(74) *Attorney, Agent, or Firm*—Pepper Hamilton LLP

(57) ABSTRACT

The invention relations to a hydroxylapatite gel obtained through a sol-gel process, in which an alkaline aqueous solution of a calcium salt is reacted with an alkaline aqueous solution of a phosphate salt in a calcium and phosphorous molar ratio in the range of 1.67 to obtain a sol. The sol is then transformed into a gel by hydrothermal treatment. The hydroxylapatite gel thus obtained exhibits excellent properties for use as a binding agent in moldable hydroxylapatite materials, comprising a granular filling material containing calcium in addition to the gel. The filling material is also preferably a hydroxylapatite material. Shaped bodies can be obtained from the hydroxylapatite material, which are most suitable for use in bone surgery as filtering materials. The invention further relates to a metal implant comprising a coating of the inventive hydroxylapatite material. The invention also concerns a method for producing the hydroxylapatite gel, the shaped bodies and the coated metal implant.

15 Claims, No Drawings

HYDROXYLAPATITE GEL

RELATED APPLICATIONS

This application is a continuation of International Application No. PCT/EP98/03093, filed May 26, 1998, which in turn claims priority to Bulgarian Application No. 101544, filed May 30, 1997 both of which are incorporated herein by reference.

The invention relates to a hydroxylapatite gel, to compositions and moldings containing the latter, and to the use thereof, especially in the area of bone surgery.

There is a need in the area of bone surgery for bone substitutes and implants which are tolerated by the body and easy to process. In order to facilitate taking of the bone implant in the body it should have a structure which is as similar as possible to that of bone. In addition, high mechanical stability is desirable. The implant material should moreover be suitable as carrier for active substances such as, for example, growth-promoting or -inhibiting substances.

One proven bone substitute material is a hydroxylapatite material obtained from the calcium carbonate skeleton of calcareous algae. A material of this type is described in DE 37 09 897 C2. To produce moldings, the granular hydroxylapatite material obtained by hydrothermal synthesis is shaken into a molding with slaked lime as binder and then subjected to another hydrothermal treatment. The bone implant obtained in this way has a high interconnective porosity and a high specific surface area. In its chemical makeup and crystalline structure it is considerably more similar to bone than are other bone substitute materials. However, in some specific applications, bone substitute materials having an even greater porosity and particularly high mechanical stability are necessary.

It is an object of the invention to indicate materials which are suitable for producing a bone substitute material which is as similar as possible in its chemical makeup and the crystalline structure to natural bone, has a very porous microstructure but, at the same time, has high mechanical stability. The materials should be simple to produce, cost-effective and easily processable. In addition, they should permit specific adjustment to the proportion of crystalline phases and the strength of the bone substitute material during their processing.

This object is achieved with the hydroxylapatite gel as claimed in claim 1. This hydroxylapatite gel is an essential constituent of the moldable hydroxylapatite composition as claimed in claim 9 and of the compacted hydroxylapatite composition as claimed in claim 15, which are in turn constituents of the novel hydroxylapatite molding as claimed in claim 16. The invention further relates to the use of the hydroxylapatite molding as claimed in claim 17. The hydroxylapatite molding is likewise present as coating in a metal implant as claimed in claim 20. The invention additionally relates to a process for producing the metal implant as claimed in claim 21, to a process for producing the hydroxylapatite gel as claimed in claim 23, and to a process for producing the hydroxylapatite molding as claimed in claim 28.

Further process variants and embodiments are evident from the dependent claims.

In a first aspect, the invention relates to a hydroxylapatite gel which is obtainable by a sol-gel process. This entails an alkaline aqueous solution of a calcium salt being reacted with an alkaline aqueous solution of a phosphate salt initially to give a sol. The stoichiometry is in this case chosen so that the ratio of calcium to phosphorus corresponds to the ratio in the hydroxylapatite. The molar ratio of calcium to phosphorus for producing the sol is thus in the region of about 1.67. Subsequently, the sol obtained in this way is converted into a gel by hydrothermal treatment.

The pH during the sol production is preferably in a range from 9 to 12 and particularly expediently between 10.5 and 11. The desired pH range can be adjusted by adding conventional bases. Ammonia is particularly suitable for this purpose. It has additionally emerged as advantageous initially to adjust the two aqueous solutions separately to the required pH and, if necessary, bring the pH into the desired range again after mixing the two solutions.

The sol is advantageously produced at a temperature in the range between 10° and 40° C., particularly expediently at room temperature (20° to 25° C.)

It is possible to use for producing the sol for example 0.1 to 1 N aqueous solutions of the calcium salt and of the phosphate salt. 0.3 to 0.5 N aqueous solutions of the salts are particularly suitable.

It is possible to employ as starting materials all soluble calcium and phosphate salts, which should where possible contain no constituents not tolerated by the body. An example of a suitable calcium salt is calcium nitrate. Diammonium hydrogen phosphate can be used as phosphate salt.

Under the stated conditions, after the two aqueous solutions have been mixed they are left to stand for a period of several days to form the sol. In a second step, the sol is then converted by hydrothermal treatment into a gel. The hydrothermal treatment expediently takes place at a temperature in the range from 180 to 200° C. It is particularly advantageously carried out in an autoclave. Autoclaves coated with polytetrafluoroethylene or similar inert linings are particularly suitable. It is advantageous for the autoclave to be no more than two-thirds full and for the hydrothermal treatment to be carried out under the saturation vapor pressure of the solution which is then set up. The pH during the conversion to the gel is advantageously in the same range as for the production of the sol, that is to say between 9 and 12 and, in particular, between 10.5 and 11.

During the hydrothermal treatment there is formation of crystal nuclei and fine crystals of hydroxylapatite in the sol. Specific control of the proportions of crystalline phases in the hydroxylapatite gel is possible depending on the duration of the hydrothermal treatment. The physical properties of the hydroxylapatite gel can be specifically influenced in this way. The hydrothermal treatment advantageously lasts until the proportion of crystal nuclei and microcrystalline hydroxylapatite in the gel is above 80% and, in particular, about 90%. Up to two-thirds of the water present in the sol remains in the gel composition. The novel gel normally contains up to 70% by weight of water after its production. An average water content is. about 60% by weight. If the hydroxylapatite gel is left to stand for a longer time, the gel separates out and an aqueous supernatant forms. The water content of the gel can, if desired, be reduced specifically by pouring off this supernatant.

The novel hydroxylapatite gel is outstandingly suitable as binder and can be employed, for example, for producing bone substitute materials and filter materials. Compared with conventional binders, the advantage of the novel hydroxylapatatite gel is that the crystalline phase structure adjusted during its production is retained in the final product, and final materials with a very porous microstructure are obtained. In addition, the novel hydroxylapatite gel ensures excellent moldability of the compositions containing it, whose density can be specifically influenced by compression.

In a further aspect, the invention relates to a moldable hydroxylapatite composition which, besides the novel hydroxylapatite gel which acts as binder, comprises a calcium-containing granular filler. Examples of suitable fillers are all those which are already employed in the area of bone surgery. Hydroxylapatite materials obtained from calcareous algae are particularly suitable as granular filler. Examples are described in German Patent 37 09 897. The calcium carbonate skeleton of the algae is retained in the materials described therein, so that the material has a high interconnective porosity and a large specific surface area.

It is also possible to use as granular filler for the moldable hydroxylapatite composition a modified tricalcium phosphate-containing hydroxylapatite material which is obtainable by reacting an algal hard tissue, from which organic compounds have been removed, in an alkaline aqueous phosphate solution with addition of $Mg^{2+}$ ions at elevated temperature. A material of this type is described in a parallel German patent application by the applicant. This tricalcium phosphate-containing hydroxylapatite material advantageously has a tricalcium phosphate content of from 20 to 90% by weight. The algal hard tissue is, as in the case of the unmodified hydroxylapatite materials, expediently obtained from calcareous marine algae, in particular from those of the species Corallinacea or Codiacea.

The novel hydroxylapatite gel and the granular solid can be mixed together in a wide ratio of amounts in the moldable hydroxylapatite composition. Suitable ratios of hydroxylapatite gel and granular solid are, for example, between 10:1 and 1:10 by weight, starting in this case from a hydroxylapatite gel with a water content of about 60% by weight. The proportions in each case are chosen in accordance with the desired subsequent use of the novel moldable hydroxylapatite composition. The manner in which the moldable composition is to be processed also plays a part in the selection of the proportions of the two components. On use of the novel moldable hydroxylapatite composition for coating, higher proportions of gel may facilitate the processing. Moldings consisting only of hydroxylapatite composition—for example bone substitute materials, which must have high mechanical strength—will normally contain a larger proportion of granular solid. It is possible to use for the latter, for example, ratios of gel to solid between 1:5 and 1:8 by weight.

The novel moldable hydroxylapatite composition may contain further components such as those which are usual, for example, in bone substitute materials or filter materials. For a bone substitute material, it may be expedient, for example, to add at least one active substance to the composition. Examples are growth-promoting or—inhibiting substances. Specific examples are antibiotics, chemotherapeutic agents, tumor-inhibiting compounds and bone-inductive substances. Bone morphogenic proteins may be mentioned to exemplify the latter. These active substances can be incorporated into the novel composition, or they are applied to the finished molding produced from the novel composition. It is expedient to use for each active substance the respective clinically active amount.

The novel moldable hydroxylapatite composition can, owing to its proportion of novel hydroxylapatite gel, be molded as desired. This considerably facilitates the production even of moldings with a complicated structure. If a hydroxylapatite material obtained from calcareous algae is used as granular filler, the resulting moldable composition consists almost exclusively of hydroxylapatite. Not only are moldings produced from this composition exceptionally well tolerated by the body, they also have an extremely porous microstructure with, at the same time, high mechanical stability. The novel hydroxylapatite composition is therefore exceptionally suitable for producing bone substitute materials. In addition, the physical properties of the moldable composition and, as a consequence, also of the moldings produced therefrom can be specifically influenced. For example, it is possible to compress the hydroxylapatite composition under pressure and thus increase its density and its strength. Use of a pressure not exceeding 1 MPa for the compression leads to retention of the porous microstructure of the composition.

Reference has already been made to the control of the proportions of crystalline phases in the gel—and thus also in the moldable hydroxylapatite composition containing the gel. The crystallinity can also be influenced by the nature and duration of the thermal treatment of the moldable hydroxylapatite composition with which a solid molding is produced from the composition.

For this purpose, the novel moldable hydroxylapatite composition is introduced into a suitable mold and expediently firstly degassed before setting. Treatment with ultrasound is suitable, for example, for this purpose. To obtain a higher density and greater strength, the moldable composition can be compressed, as mentioned. The thermal treatment for setting the composition expediently takes place at a temperature in the range between 500° and 650° C., in particular between 550° C. and 600° C. The duration of the thermal treatment depends on the composition of the moldable composition and the size of the molding. The treatment time will normally be between about half an hour and several hours. If necessary, the novel molding produced can be subsequently processed with conventional surgical implements to bring it into its final shape. It is additionally possible to apply coatings to the novel hydroxylapatite molding, such as those of bone-inductive compounds already mentioned.

Because of the very porous microstructure associated with great mechanical strength, the novel hydroxylapatite molding according to the invention is outstandingly suitable for use in the field of bone surgery, in particular as bone substitute material or as carrier material for active substances. Because of their porous structure, the novel moldings can, however, also be employed as filter materials.

The novel hydroxylapatite moldings are additionally suitable as bioactive coating on metal implants and, in particular, on titanium bone implants. The invention relates in a further aspect to a metal implant of this type comprising a coating of the novel hydroxylapatite molding. To produce the implant, a layer of the novel moldable hydroxylapatite composition is applied to the metal surface and is subjected to a thermal treatment at between 500° and 650° C., as has been described above. In order to improve the adhesion of the coating to the metal surface, this surface is expediently treated before coating thereof. Treatments of this type for improving adhesion are known for metal implants. These known surface treatment processes can also be used before application of the novel coating. However, a treatment to which this invention likewise relates is preferably carried out.

In the preferred novel process for producing a metal implant, the surface of the metal is, before application of the coating, oxidized in an electrolyte solution with spark discharge at a temperature between −10 and −20° C. until the thickness of the oxide layer is between 25 and 40 μm. The oxidation takes place with 50 Hz alternating current and with a voltage of between 110 and 200 V. The aqueous electrolyte solution used comprises:

| polyethylene glycol (molecular weight 200 to 400) | 80 to 200 ml/l |
|---|---|
| at least one chlorine oxoacid or salt thereof and | 5 to 20 g/l |
| amine and/or | 10 to 30 ml/l |
| hydrofluoric acid or salts thereof and/or | 2 to 25 g/l |
| phosphoric acid or salts thereof and/or | 20 to 80 g/l |
| perboric acid or salts thereof | 10 to 40 g/l |

The oxidizing agents preferably used are the alkali metal salts of chlorine oxoacids, in this case especially the chlorates and chlorites such as sodium chlorate or sodium chlorite. It is also possible to use mixtures of different salts. The alkali metal or ammonium salts of the other acids are preferably used. Examples of preferred compounds are sodium fluoride, ammonium fluoride, potassium dihydrogen phosphate and sodium perborate.

Aliphatic amines or alcohol amines are expediently employed as amine, preferably triethylamine or triethanolamine.

The oxide layer obtained by the novel process is subsequently recrystallized in a combustion process. It is expedient for the oxide layer after drying to be exposed to a temperature of from 550 to 650° C. for 20 to 40 minutes. It is advantageous to remove any unbound ions still present on the oxide layer with distilled water before the novel moldable composition is applied to the treated metal surface. The layer thickness is expediently from 5 to 10 μm. The thermal treatment of the moldable composition takes place as described above.

The invention is to be explained further hereinafter by means of a few examples.

EXAMPLE 1
Production of the Hydroxylapatite Gel

A 0.5 N aqueous solution of $Ca(NO_3)_2 \cdot 4H_2O$ and a 0.3 N aqueous solution of $(NH_4)_2HPO_4$ are separately adjusted with ammonia to a pH of 10.5. The two solutions are thoroughly mixed in the ratio 1:1 by stirring. The pH of the solution obtained in this way is, if necessary, returned to 10.5 with ammonia.

The reaction mixture is left to stand at a temperature between 20° and 25° C. for 5 to 6 days. During this time, an initial apatite sol forms.

A gel is produced by hydrothermal treatment of the sol at 180 to 200° C. To do this, the gel is transferred into a PTFE-lined autoclave which is not more than two-thirds full. The hydrothermal treatment takes place under the saturation vapor pressure of the solution. The treatment is continued until at least 80% crystal nuclei and microcrystalline hydroxylapatite have formed. It is preferable to continue the hydrothermal treatment until about 90% crystal nuclei and microcrystalline hydroxylapatite have formed. The hydrothermal treatment normally takes at least 24 hours. After a reaction time of about 30 hours no further significant changes in the crystallinity are observed. The resulting hydroxylapatite gel has a water content of about 60% by weight.

EXAMPLE 2
Production of a Moldable Hydroxylapatite Composition

The hydroxylapatite gel obtained in Example 1 is mixed in a ratio of 1:10 by weight with a granular hydroxylapatite material produced from calcareous red algae as described in German Patent 37 09 897. A homogeneous pasty composition is obtained.

EXAMPLE 3
Production of a Hydroxylapatite Molding

The hydroxylapatite composition obtained in Example 2 is introduced into a compression mold. It is de-aerated by exposure to ultrasound and compacted under a pressure of about 0.9 MPa for a few minutes. The compacted composition in the compression mold then undergoes thermal treatment in a furnace at 550 to 600° C. for about 60 minutes. This results in a molding with a very porous microstructure and great mechanical strength. Subsequent mechanical processing thereof is possible.

EXAMPLE 4
Production of a Hydroxylapatite-coated Metal Implant

1. Pretreatment of the Metal Implant

A titanium bone implant is oxidized with spark discharge in an electrolyte solution at −10° C. The solution contains:

| polyethylene glycol (MW 200) | 100 ml/l |
|---|---|
| sodium chlorate/chlorite | 5 g/l |
| sodium fluoride | 21 g/l |
| potassium dihydrogen phosphate | 68 g/l |
| triethylamine | 10 ml/l |

The oxidation is carried out with a voltage of 160 V for 5 minutes. The treated implant is then removed from the solution, and the produced oxide layer is recrystallized in a furnace at 600° C. for 20 minutes. It is then washed several times with boiling distilled water until all unbound ions have been completely removed from the implant.

2. Pretreatment of the Metal Implant ($2^{nd}$ Variant)

The surface of the titanium bone implant is oxidized with spark discharge in an electrolyte solution at −15° C. The solution consists of:

| polyethylene glycol (MW 400) | 150 ml/l |
|---|---|
| sodium chlorate/chlorite | 10 g/l |
| sodium fluoride | 21 g/l |
| potassium dihydrogen phosphate | 68 g/l |
| sodium perborate | 38 g/l |
| ammonium fluoride | 6 g/l |
| triethanolamine | 15 ml/l |

The process is carried out as in section 1 but with a voltage of 180 V for 3.5 minutes. The oxide layer undergoes recrystallization analogously to section 1 at 580° C. for 30 minutes. The subsequent treatment likewise corresponds to that in section 1.

3. Application of the Coating

The metal implant treated as in section 1 or 2 is provided with a coating which consists of a hydroxylapatite gel produced as in Example 1 and of hydroxylapatite granules as described in German Patent 37 09 897 in a ratio of 2:0.75 by volume. The layer thickness is about 7 μm. After the layer has been dried it is fixed in a furnace at 550° C. for 40 minutes.

4. Application of the Coating (Variant 2)

The procedure is as described in section 3 but the ratio of hydroxylapatite gel to granules is 2:1. Fixation of the layer takes place at 500° C. for 30 minutes.

The result in both cases is a coating with exceptionally good bioactive properties. The coating is bonded satisfactorily to the metal surface. In clinical investigations, the novel coated metal implant revealed extremely favorable conditions for bone augmentation and good fixation of the newly formed bone tissue to the surface.

What is claimed is:

1. A moldable hydroxylapatite composition, which comprises a calcium-containing granular filler and a hydroxylapatite gel which is obtainable by a sol-gel process in which an alkaline aqueous solution of a calcium salt is reacted with an alkaline aqueous solution of a phosphate salt with a molar ratio of calcium to phosphorus in the region of 1.67 to give a sol, and the sol is converted by hydrothermal treatment into a gel.

2. A moldable hydroxylapatite composition as claimed in claim 1, wherein the pH during the production of the sol is in a range from 9 to 12 and, in particular, from 10.5 to 11.

3. A moldable hydroxylapatite composition as claimed in claim 1, wherein the sol is produced at from 10° C. to 40° C. and, in particular, at from 20° C. to 250° C.

4. A moldable hydroxylapatite composition as claimed in claim 1, wherein 0.1 to 1 N aqueous solutions of the calcium salt and of the phosphate salt and, in particular, 0.3 to 0.5 N aqueous solutions are employed.

5. A moldable hydroxylapatite composition as claimed in claim 1, wherein calcium nitrate is employed as the calcium salt.

6. A moldable hydroxylapatite composition as claimed in claim 1, wherein diammonium hydrogen phoshate is employed as the phosphate salt.

7. A moldable hydroxylapatite composition, which comprises a calcium-containing granular filler and a hydroxylapatite gel which is obtainable by a sol-gel process in which an alkaline aqueous solution of a calcium salt is reacted with an alkaline aqueous solution of a phosphate salt with a molar ratio of calcium to phosphorus in the region of 1.67 to give a sol, and the sol is converted by hydrothermal treatment into a gel, wherein the hydrothermal treatment takes place at from 180° C. to 200° C.

8. A moldable hydroxylapatite composition as claimed in claim 7, wherein the hydrothermal treatment takes place until the proportion of crystal nuclei and microcrystalline hydroxylapatite is above 80% and, in particular, about 90%.

9. A moldable hydroxylapatite composition, which comprises a calcium-containing granular filler and a hydroxylapatite gel which is obtainable by a sol-gel process in which an alkaline aqueous solution of a calcium salt is reacted with an alkaline aqueous solution of a phosphate salt with a molar ratio of calcium to phosphorus in the region of 1.67 to give a sol, and the sol is converted by hydrothermal treatment into a gel, wherein a hydroxylapatite material obtained from calcareous algae is used as the granular filler.

10. A moldable hydroxylapatite composition as claimed in claim 9, wherein a tricalcium phosphate-containing hydroxylapatite material which is obtainable by reacting an algal hard tissue, from which organic compounds have been removed, in an alkaline aqueous phosphate solution with addition of $Mg^{2+}$ ions at elevated temperature is used as granular filler.

11. A moldable hydroxylapatite composition as claimed in claim 10, wherein the tricalcium phosphate content is from 20 to 90% by weight based on the granular filler.

12. A moldable hydroxylapatite composition as claimed in claim 8, wherein hydroxylapatite gel and the granular filler are present in a ratio of from 10:1 to 1:10 and, in particular, from 1:5 to 1:8 by weight.

13. A moldable hydroxylapatite composition, which comprises a calcium-containing granular filler and a hydroxylapatite gel which is obtainable by a sol-gel process in which an alkaline aqueous solution of a calcium salt is reacted with an alkaline aqueous solution of a phosphate salt with a molar ratio of calcium to phosphorus in the region of 1.67 to give a sol, and the sol is converted by hydrothermal treatment into a gel, which further comprises at least one active substance, in particular a growth-promoting or growth-inhibiting compound, an antibiotic, a chemotherapeutic agent, a tumor-inhibiting compound or a bone-inductive compound, in particular at least one bone morphogenic protein.

14. A compacted hydroxylapatite composition obtainable by compression under a pressure of up to 1 MPa of a moldable hydroxylapatite composition, which comprises a calcium-containing granular filler and a hydroxylapatite gel which is obtainable by a sol-gel process in which an alkaline aqueous solution of a calcium salt is reacted with an alkaline aqueous solution of a phosphate salt with a molar ratio of calcium to phosphorus in the region of 1.67 to give a sol, and the sol is converted by hydrothermal treatment into a gel.

15. A hydroxylapatite molding obtainable by thermal treatment at a temperature of from 500° C. to 650° C. and, in particular, from 550° C. to 600° C., of a moldable hydroxylapatite composition, which comprises a calcium-containing granular filler and a hydroxylapatite gel which is obtainable by a sol-gel process in which an alkaline aqueous solution of a calcium salt is reacted with an alkaline aqueous solution of a phosphate salt with a molar ratio of calcium to phosphorus in the region of 1.67 to give a sol, and the sol is converted by hydrothermal treatment into a gel.

* * * * *